United States Patent [19]

Skov et al.

[11] Patent Number: 4,550,085
[45] Date of Patent: Oct. 29, 1985

[54] METHOD OF DETECTING OR DETERMINING HISTAMINE IN HISTAMINE CONTAINING MATERIALS

[76] Inventors: Per S. Skov, Kanslergade 6 st., 2100 Copenhagen O; Svend Norn, Skovvang 1, 3460 Birkerød; Bent Weeke, Tollosevej 20, 2700 Brønshøj, all of Denmark

[21] Appl. No.: 300,262

[22] Filed: Sep. 8, 1981

[30] Foreign Application Priority Data

Jul. 6, 1981 [DK] Denmark .............................. 2982/81

[51] Int. Cl.⁴ ...................... G01N 33/48; G01N 33/58
[52] U.S. Cl. .......................................... 436/98; 435/7; 436/527; 436/541; 436/804; 436/807; 436/811
[58] Field of Search ................... 436/86, 98, 807, 811, 436/527, 541, 804; 435/7

[56] References Cited

U.S. PATENT DOCUMENTS

| | | | |
|---|---|---|---|
| 4,014,651 | 3/1977 | Bettinger et al. | 436/500 |
| 4,020,151 | 4/1977 | Bolz et al. | 424/230 |
| 4,256,693 | 3/1981 | Kondo et al. | 422/56 |
| 4,297,337 | 10/1981 | Mansfield et al. | 436/526 X |

FOREIGN PATENT DOCUMENTS

| | | |
|---|---|---|
| 525394 | 11/1982 | Australia . |
| 1242493 | 8/1971 | United Kingdom . |
| 2053022 | 2/1981 | United Kingdom . |

OTHER PUBLICATIONS

Bosse et al., Med. Pharmacol. Exp. 16:459–461, (1967).

*Primary Examiner*—Arnold Turk
*Attorney, Agent, or Firm*—Darby & Darby

[57] ABSTRACT

Histamine is detected or determined selectively in a sample by causing the sample to contact glass microfibers in such a quantitative proportion as will permit the histamine present to bind to the fibers. The amount of bound histamine may be determined by competitive determination in the presence of labelled histamine on the basis of a standard curve, or may be determined directly by conventional coupling reactions.

The method is simple and particularly useful for allergy diagnostics because it exhibits good correlation with known fluorometric methods.

6 Claims, 5 Drawing Figures

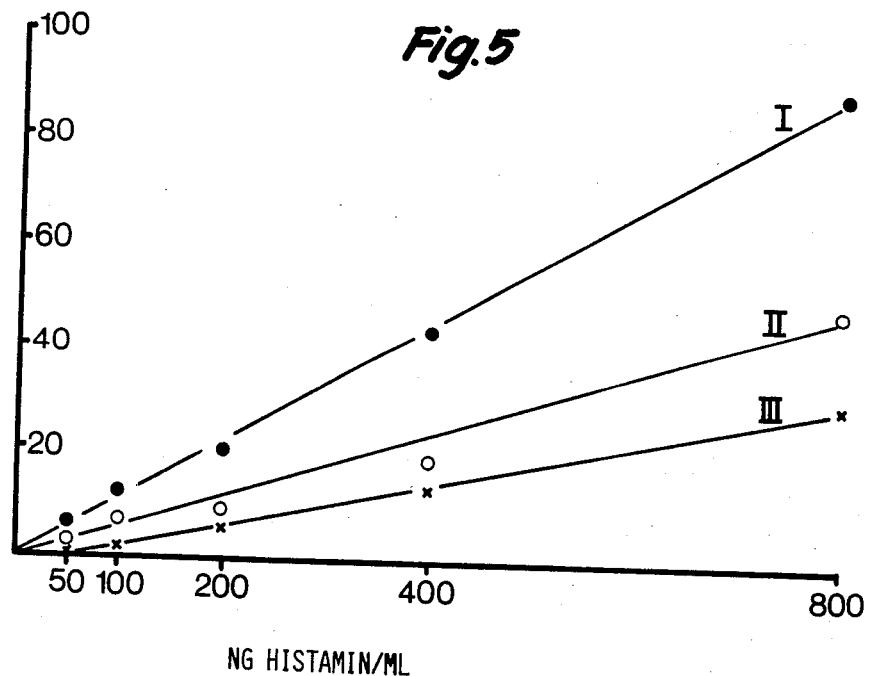

METHOD OF DETECTING OR DETERMINING HISTAMINE IN HISTAMINE CONTAINING MATERIALS

FIELD OF THE INVENTION

The present invention relates to a method of detecting or determining histamine in histamine-containing materials, particularly blood or blood fractions. The invention also relates to an analytical agent to be used in the performance of the method.

BACKGROUND OF THE INVENTION

One of the problems in the treatment of allergic diseases is the lack of diagnostic techniques which are sufficiently specific and sensitive and which do not imply any risk to the patient. Furthermore, there is a need for a rapid, simple, and inexpensive diagnostic technique which would ensure a decrease in the number of patients now waiting for adequate treatment.

In human blood and tissue there exist specific cells (basophil leucocytes and mast cells) which are involved in the allergic reaction. On the surface of these cells is a distinct class of antibodies (IgE-antibodies). When e.g. a patient is allergic to cat, an allergic reaction is caused by the antibodies on the surface of these cells which specifically recognize the protein structure of cat dandruff. When inhaled, cat protein comes in contact with the mast cells and the basophil leucocytes of the lung tissue. The antibodies on the cell surface will react with cat protein, thereby triggering a reaction in the cell, which in turn causes the release of a number of substances (allergic mediators). These allergic mediators are responsible for the symptoms of the patient.

For many years it has been possible to imitate the allergic reaction in vitro. This is done by exposing a blood sample from the allergic patient to e.g. cat protein. Allergic mediators are released from the basophil leucocytes in the blood sample. Of these mediators it is possible to determine one substance, i.e. histamine. Therefore, if the patient is allergic to cat, it is possible to determine the release of histamine from the cells. Methods based on this principle represent the best assay for obtaining a correct diagnosis, and are explained in detail below.

By means of histamine determination it is possible to diagnose the responsible antigens (e.g. grass pollen, animal dandruff, drugs, foodstuffs, mold fungi, and bacteria) in patients with allergic diseases (asthma, urticaria, and hay fever).

A general problem of this test is that it is difficult to perform in the laboratory. Few tests can be performed daily and the demand for laboratory technicians is high. Therefore, a simplification of the test is greatly needed so that it could be introduced in the daily diagnostic routine of the clinic.

As mentioned, a number of assays exist for detecting histamine in liquids. Thus, the original histamine determination was described by Shore et al. and was based on a fluorometric assay (ref. 1).

The principle of this assay described in Hoppe-Seyler's 2. Physiol. Chem. 353: 911-920, 1972, is a coupling of histamine to a fluorophore (o-phthalaldehyde), whereby a ring structure is formed. The concentration of this ring structure, which can be determined spectrophotometrically, depends on the amount of histamine present. The method was later been modified to increase specificity and sensitivity. Stahl Skov & Norn, Acta Allergol. 32: 170-182, 1977, (ref. 2) have thus simplified the assay by allergen-provocation of Ficoll-Hypaque-isolated cell suspensions containing 0.5-2% basophil leucocytes instead of whole blood. By fractionation of the blood, interfering substances are removed, so that the histamine content of the basophil leucocytes can be determined directly, avoiding a long extraction procedure. However, the fractionation procedure (gradient centrifugation) necessary to remove interfering substances is time consuming and difficult to perform, and Siraganian therefore developed an autoanalytical fluorometric method Int. Archs Allergy appl. Immun. 49: 108-110, 1975. This method is used in the clinic, but has only found limited application, due to its demand for technical experience, constant monitoring, and expensive apparatus.

Taylor et al. Int. Archs Allergy appl. Immun. 61: 19-27, 1980 has developed another assay for determining histamine in biological material. This very sensitive and specific method is an enzymatic isotope technique based on methylation of histamine by means of N-methyltransferase. This assay is useful in determining small amounts of histamine in tissue, blood, and urine. However, the need for a routine method to be used in the clinic is not satisfied by this method since the number of assays that can be performed in a day is low (approx. 30) and the assay time is long.

Stahl Skov et al. Allergy 34: 261-263, 1979, have developed another method based on in vitro incorporation of radioactively labelled histamine in the basophil cells of the patient, where the release of labelled histamine is determined after provocation with the suspected allergens.

However, as illustrated below, a poor correlation with the release of histamine determined fluorometrically was obtained by this method.

SUMMARY OF THE INVENTION

The purpose of the present invention is to provide a method for the detection or determination of histamine, which is not vitiated by the drawbacks of the known methods such as apparatus requirements, time consumption, and pretreatment of blood samples.

In particular, it is the purpose of the present invention to provide a simple and specific method for the detection and determination of histamine in histamine-containing materials, which is rapid and easy to perform, which requires only a small amount of material, and which does not make heavy demands on the training of personnel.

This is achieved by the method of the invention, which comprises: contacting a sample of the material with glass microfibers in such quantitative proportions between the glass microfibers and the material as will permit the histamine concentration to be detected or determined or to be bound to the microfibers; and registering or measuring the bound amount of histamine. As mentioned, the invention also relates to an agent for use in the performance of the method, and this agent is characterized by comprising glass microfibers deposited onto a carrier.

DETAILED DESCRIPTION

Figure 1:
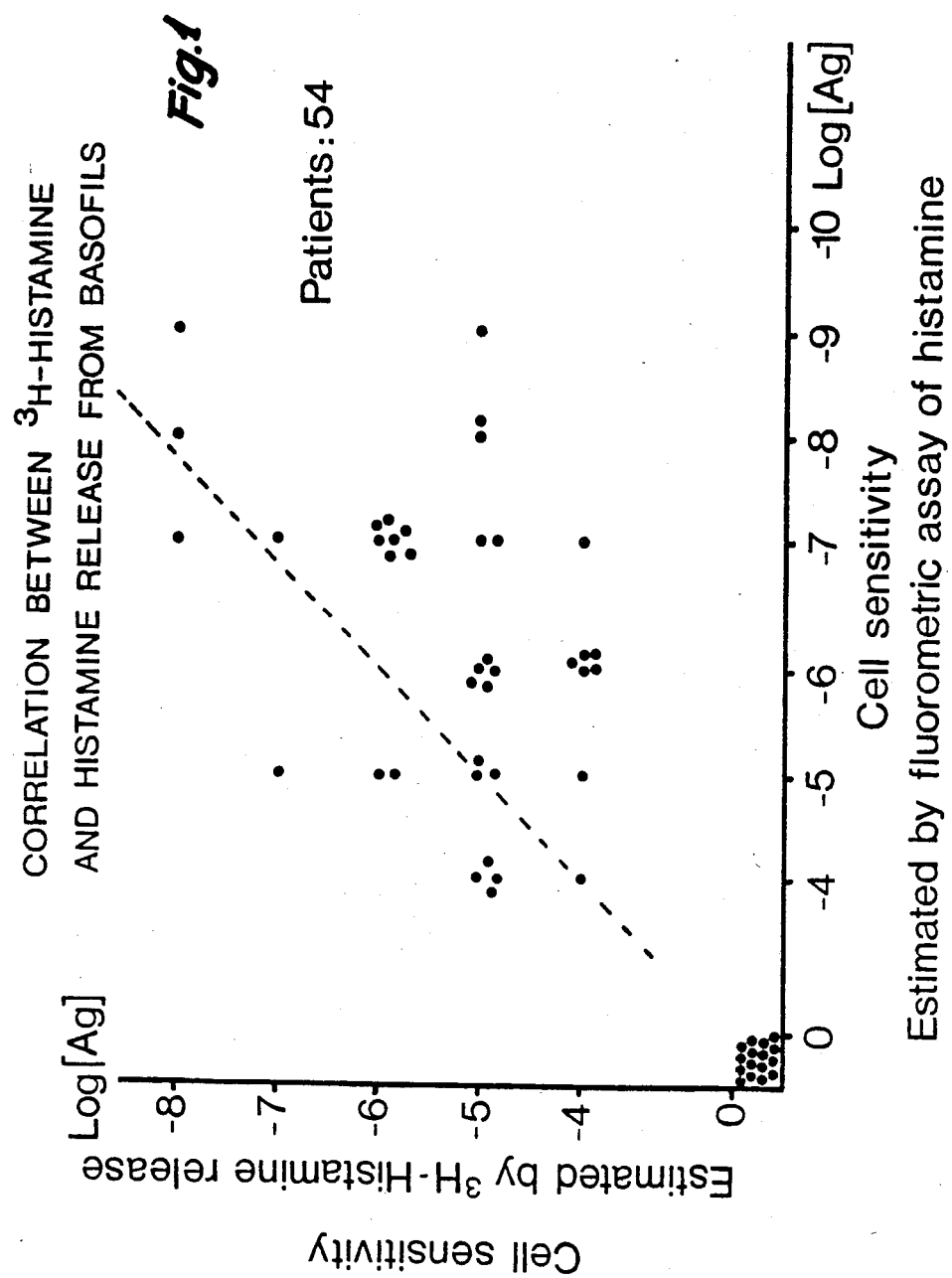

The invention is based on the surprising finding that histamine is selectively bound to glass microfibers even after repeated washings. Glass microfibres are extensively used as filters and described in detail, e.g. in the brochure "Glass Microfibre Filters", Publication No. 630, Whatman, Springfield Mill, Maidstone, Kent, England, which is incorporated by reference. In this brochure it is emphasized that the microfibers exhibit extremely low adsorption capacity, but have in a few cases been used as a means to adsorb high molecular substances, especially proteins, such as albumin and poly-U in RNA assays.

The binding of histamine to the glass microfibers is surprising because histamine does not bind to cellulose fibers, dextran gels of the "Sephadex ®" type or aluminium hydroxide gells whose high adsorption capacity is well-known.

The binding is even more surprising because low molecular compounds such as serotonin and histidine as well as the histamine metabolites 1,4- and 1,5-methyl imidazole acetic acid do not bind to the fibers, which is demonstrated below.

Glass microfibers are commercially available and are non-toxic and not dangerous to use. A glass microfibers filter marketed under the trade mark "Whatman ®GF/B" has been found to be very suitable for the performance of the present assay. Also "Whatman ®GF/C" microfibers may be used, but this type has more variable binding properties.

It appears from the above-mentioned brochure that the said fibers are boron silicate fibers with the following typical oxide content:

| | % | | % |
|---|---|---|---|
| $SiO_2$ | 57.9 | CaO | 2.6 |
| $B_2O_3$ | 10.7 | MgO | 0.4 |
| $Fe_2O_3$ | 5.9 | BaO | 5.0 |
| $Al_2O_3$ | 10.1 | ZnO | 3.9 |
| $Na_2O$ | | F | 0.6 |
| $K_2O$ | 2.9 | | |

The invention is of course not restricted to the use of glass microfibers of the above-mentioned types, and the skilled person will be able to find fibers of optimal binding properties among the commercially available glass fiber types by simple binding tests, as described below in example 1.

However, it is believed at present that the most suitable glass microfibers are those of the type "Whatman GF/B" and fibers of similar properties, particularly binding properties. To obtain the desired sensitivity, the glass microfibers are advantageously divided into fine particles as small as 2 to 20 μm, before they are used in the method of the invention. Here too, the most appropriate fiber dimension and degree of disintegration can be determined by tests and also depends on the carrier onto which the fibers are to be deposited to provide the most expedient assay. Another factor to be considered in selecting fiber dimension is the type of sample material to be tested.

The quantitative proportion between the glass microfibres and the histamine-containing material can likewise be determined by tests depending upon the amount of histamine expected to be bound to the fibers. The amount of histamine released at various degrees of allergy is well-known from the literature, so that standard curves for predetermined histamine amounts may be plotted and serve as a basis for determination of the amount of histamine in an unknown sample, e.g. by a competitive determination, as explained in detail below.

A suitable carrier type is a tube of glass or particularly plastic in the form of a small test tube, but also glass sheets, foils or strips may be used. For allergy diagnostics, the glass fibers may advantageously be deposited onto suitable carriers together with test allergens and made up into suitable test devices, e.g. in the form of diagnostic kits.

The method of the invention is particularly useful for the detection or determination of histamine released as a consequence of an allergic reaction, in which a blood sample is to be used as the test material. In addition to the general advantages explained in the foregoing, the method provides a significant advantage over the known methods in that it is sufficient to remove the blood plasma, e.g by centrifugation and washing with a physiological buffer. If desired, the red blood cells (erythrocytes) may also be removed, which can be done simply e.g. with the sedimentation by addition of dextran.

The method can also be used for detection or determination of histamine in other body fluids from humans and animals, such a lymph, cerebrospinal fluids or urine, or in tissue samples or tissue extracts. In this context it is noted that histamine is released in diseases other than allergies, e.g. mastocytosis.

Finally, the method may be used for detection or determination of histamine in foodstuffs, e.g. fish such as mackerel and the like.

The registration or measurement of the histamine bound to the microfibers may be determined by different principles.

1. Competitive determination including the use of labelled histamine.
2. Direct determination.

1. Competitive determination

This principle of registration is based on a competition for the binding sites on the glass microfibers between histamine possibly present in the sample and a predetermined amount of added labelled histamine.

When plotting a standard curve for varying known concentrations of unlabelled histamine together with a given amount of labelled histamine, it is easy to determine the amount of histamine in a specific sample by adding the amount of labelled histamine used for the standard curve. This is explained more fully below in Example 1 with reference to FIG. 3.

In the following Examples 1 and 2 a radioactive isotope ($^3$H-tritium) is used for the labelling of histamine, but also other radioactive isotopes may be used, such as $^{125}$I. The bound amount of radioactively labelled histamine may be easily determined in a manner known per se, e.g. with a scintillation detection counter.

Due to the difficulty in handling radioactive materials, many new test systems have been developed in the allergy diagnostics area which comprise the use of materials other than radioactive isotopes as labelling agents. Examples of these are free radicals, fluorescent molecules (e.g. fluorescein isothiocyanate and rhodamine coloring substances), luminiscent molecules, bacteriophages, enzymes, coenzymes, and enzyme inhibitors.

It generally applies that the labelling agent is not critical, provided that the binding properties of the histamine to the fibers are not affected in a non-reproducible manner, and can be imparted to the histamine according to methods known per se. The crux of the method of the invention is the finding that histamine surprisingly binds selectively to the glass microfibers. When it has been realized in the light of this discovery that a competitive assay is possible and appropriate, it should be a matter of routine for the skilled person to test the conventional labelling methods to find the most suitable methods for the assay in question. At present the use of isotope-labelled histamine in the form of 2,5-$^3$H-histamine dihydrochloride is preferred, because this procedure is rapid and convenient and provides good accuracy and reproducibility.

2. Direct determination

The selective adsorption properties of the glass microfibers also make them suitable for direct binding of the histamine present and for subsequent determination of the bound histamine in a conventional manner, e.g. by coupling with a fluorophore compound and subsequent fluorometric measurement. This procedure is illustrated in Example 3 below.

The preparation of plastic tubes containing glass microfibers for use in the present method is easy and inexpensive (5000 to 10,000 tubes per day). The method has proved to be time-saving, as one laboratory technician can prepare about 400 samples per day, as compared with the previous maximum of 150. The method is also blood-saving, as it only requires 10 ml of blood for the determination of 8 to 10 allergies per patient, whereas the known methods require 50 ml of blood.

Figure 3:
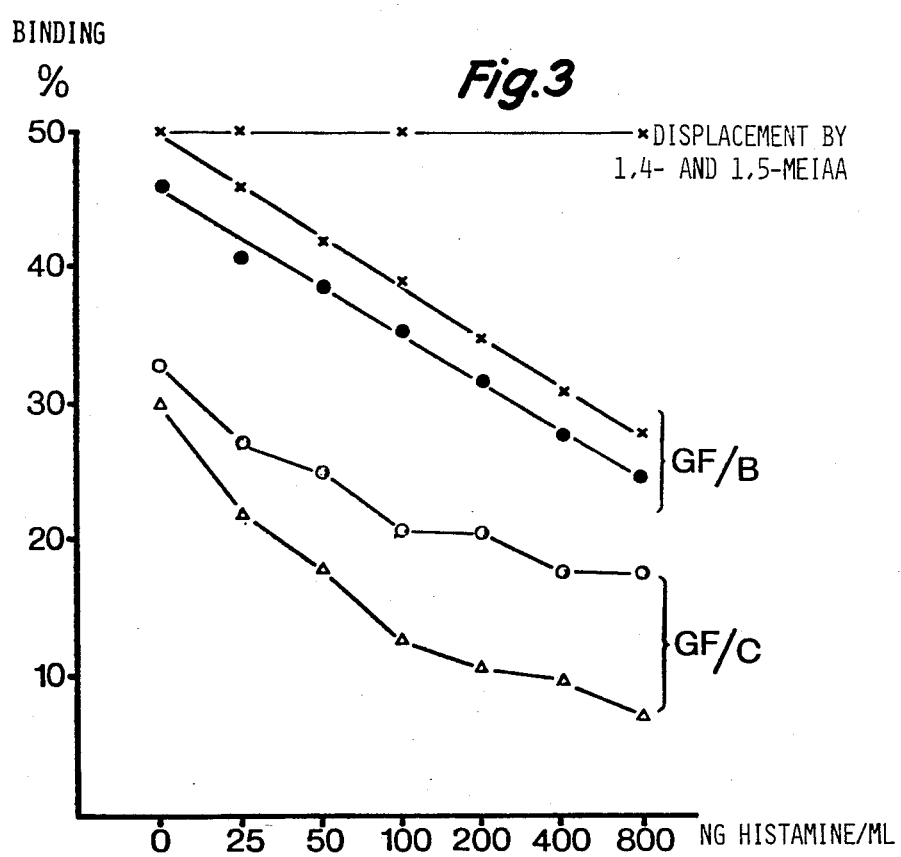
Figure 4:
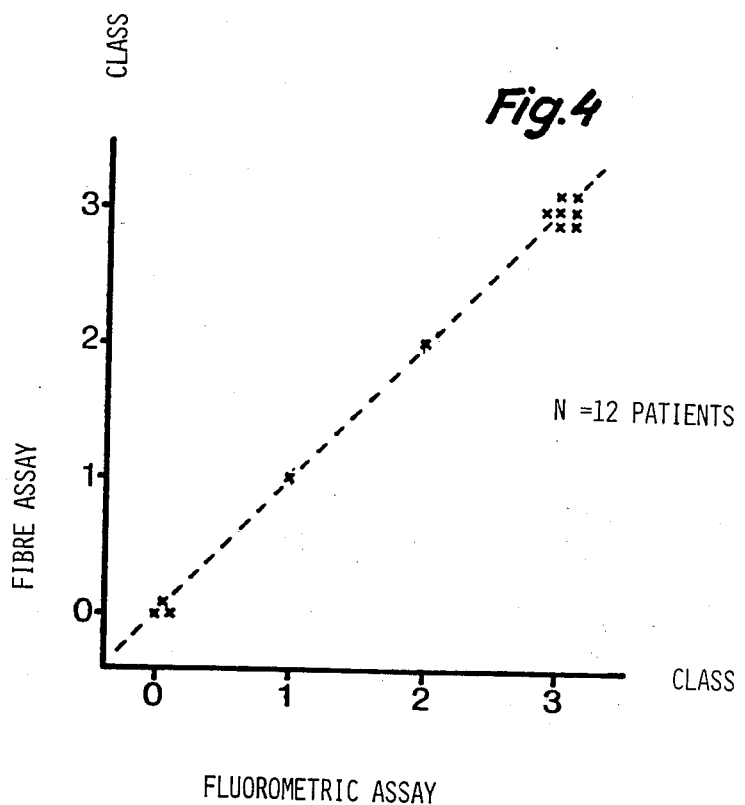

Since the method is both reproducible and specific and exhibits good correlation with fluorometric histamine determination, it is particularly useful in providing precise information about suspected allergens such as house dust, animal dandruff, pollen, mold fungi, drugs, foodstuffs, bacteria, and autoantigens. The method of the invention is illustrated in detail in the following examples with reference to the drawings, in which FIG. 1 shows a correlation between histamine determinations performed according to Stahl Skov et al. and by fluorometric assay, FIG. 2 shows the percentage of binding of tritiated histamine, histidine, and serotonin, respectively, in equimolar concentrations to glass microfibers, FIG. 3 shows the binding of varying concentrations of tritiated histamine to two different glass microfiber types after addition of known amounts of unlabelled histamine and demonstrates the lack of displacement of tritiated histamine caused by the two histamine metabolites 1,4- and 1,5-methyl imidazole acetic acid (MEIAA) and is explained in connection with Example 1, FIG. 4 shows a correlation between histamine determinations performed by the method of the invention and fluorometric assay, and is explained in connection with Example 2, and FIG. 5 shows an adapted direct fluorometric histamine determination by the method of the present invention with varying washing procedures compared with conventional determination in the absence of fibers (Stahl Skov & Norn), and is explained in connection with Example 3.

The measurements in FIG. 1 clearly confirm the lack of correlation between the method of Stahl Skov et al. and the conventional fluorometric determination. The axes show declining concentrations (dilutions) of grass pollen antigen.

Figure 2:
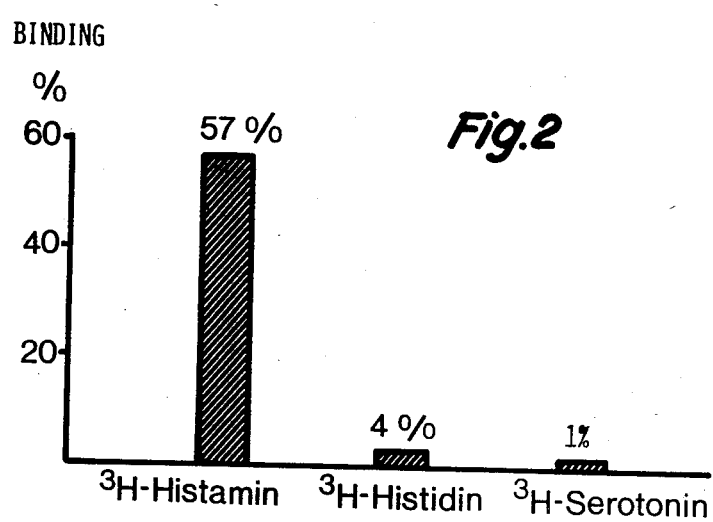

It is clearly apparent from FIG. 2 that histamine is bound surprisingly better than the low molecular compounds histidine and serotonin (5-hydroxy tryptamine). This is also of great importance to the reliability of the histamine determination since, in a number of the known methods, both compounds can interfere with histamine.

It appears from FIG. 3, which is discussed in greater detail below that the two histamine metabolites 1,4-MEIAA and 1,5-MEIAA are not bound to glass microfibers in the same concentration range as histamine, as they are not able to displace bound labelled histamine from the fibers in a competitive binding assay.

EXAMPLE 1

Preparation of glass fiber prepared tubes

"Whatman GF/B" glass fiber filters are cut into lengths of about ½ mm. 3.4 g are mixed with 500 ml of redistilled water and homogenized for 2 minutes in an "ULTRA TURRAX" blender. The crushed fibers are left for 2 hours at room temperature for sedimentation. The heavy fibers (the longest ones) precipitate, and a supernatant clearly separated from the heavy fibers and containing suspended fibers of dimensions from about 20 μm to 2 μm is removed (a total of about 100 ml) and 100 μl of this supernatant are transferred to each plastic tube. The tubes are dried in an oven at 150° C. (for 1 week), and are then taken out of the oven and are ready for use after cooling to about 20° C. With this drying procedure the glass fibers are fixed to the bottom of the tubes. The glass fiber prepared tubes have unlimited shelf life.

Plotting of standard curve for histamine determination

Known dilutions of unlabelled histamine are prepared in Tris-AMC buffer (tris-(hydroxymethyl)-amino methane 25 mM, pH 7.6, NaCl 0.12M, KCl 5 mM, CaCl$_2$ 0.6 mM, MgCl$_2$ 1.1 mM, human serum albumin 0.3 mg/ml and glucose 1 mg/ml). The histamine content was 25 ng, 50 ng, 100 ng, 200 ng, 400 ng and 800 ng/ml, respectively, and the 0-sample used was histamine-free buffer. These concentrations are used for the plotting of a standard curve. 100 μl each of these dilutions are transferred to each glass fiber prepared test tube, to which are added 10 μl of radioactively labelled histamine (2,5-$^3$H-histamine-dihydrochloride: 500 nCi/ml corresponding to 5 nCi/sample, specific activity about 53 Ci/mmole). The samples are incubated for 40 min. at 37° C. To obtain uniform results it is essential to observe the same periods of time for each sample. The samples are washed for 15 sec. with redistilled water in a cell harvester (Tech-Nunc, Roskilde, Denmark). The residual water is discarded, and 1.2 ml of Filter Count (Packard) are added. The samples are counted for 1 min. in a liquid scintillation counter, the emission of β-radiation being recorded in counts per minutes (cpm). The sample without unlabelled histamine (0-binding) contains bound labelled histamine in an amount of typically 2000 cpm, which constitutes about 60% of the total labelled histamine added to the sample. The sample containing 25 ng/ml of unlabelled histamine binds to the fibres in an amount corresponding to about 15% of the 0-binding and thus gives a count of about 1700 cpm. Increasing amounts of histamine result in an corresponding proportional decrease in cpm-linearly up to 100 μg histamine/ml.

The standard curve shown in FIG. 3 with the symbol GF/B for two parallel tests shows a semilogarithmically linear correlation between % binding, expressed as cpm (the y-axis) and histamine content (the x-axis: logarithmic). The sensitivity of the assay is about 25 ng histamine/ml. The figure shows two corresponding tests with fibers of the type "Whatman GF/C" prepared in the same manner, and these fibers exhibit a somewhat poorer correlation.

EXAMPLE 2

Determination of specific allergy to grass pollen in 12 asthmatic patients by in vitro provocation of the basophil leucocytes of the patients with grass pollen was performed 10 ml of blood are drawn from each patient by venipuncture. The blood is mixed with 0.5 ml of 0.2M EDTA (pH 7.2). The sample is divided into two parts, one of which is analyzed as described by Stahl Skov, & Norn to demonstrate the correlation between the method of the invention and fluorometric determination. 5 ml of blood are mixed with 1 ml of dextran (molecular weight 500,000 g/mol; 45 mg dissolved in 1 ml of 0.9% NaCl) to remove the erythrocytes (the red blood cells). The sample is carefully inverted and left for 30 min. at room temperature. The sedimentation of the erythrocytes is more rapid than that of the leucocytes (the white blood cells). The plasma layer containing the leucocytes is transferred to another tube and suspended in 20 ml of Tris-AMC buffer (cf. Example 1). The leucocyte suspension is centrifuged for 10 min. at 110 g of 16° C. The supernatant is removed and the cells are suspended in 20 ml of Tris-AMC buffer and centrifuged for 10 min. at 60 g and 16° C. The supernatant is again removed, and the cells are resuspended in 5 ml of Tris-AMC buffer. The cell suspension contains 2 to 4% of basophil leucocytes.

100 $\mu$l of the cell suspension are transferred to tubes prepared with glass microfibers as in Example 1. 10 $\mu$l of grass pollen are added in a 10-fold dilution series ($10^{-3}$, $10^{-4}$, $10^{-5}$ v/v) of a grass pollen standard preparation and 10 $\mu$l of isotope-labelled (tritiated) histamine are added to the tubes, corresponding to 5 nCi per sample. The samples are incubated for 40 min. at 37° C. The samples are washed for 15 sec. with redistilled water in a cell harvester (Tech-Nunc, Roskilde, Denmark). The residual water is discarded, and 1.2 ml of Filter Count (Packard) are added. The samples are counted in a liquid scintillation counter. In case of allergy to grass pollen, the basophil cells in the sample will release histamine in increasing amounts at increasing grass pollen concentrations. The released histamine is bound to the glass microfiber tubes in competition with the isotope-labelled histamine, and the binding of the isotope-labelled histamine will therefore decrease. A fall in the binding of the isotope-labelled histamine of 10% in relation to a cell sample without grass pollen is considered positive allergy to grass.

The histamine content in the unknown sample may also be calculated by the standard curve discussed in Example 1.

As appears from FIG. 4, an extremely good correlation was found between the histamine release measured by the glass microfiber method and fluorometric determination of histamine, since the investigation of 12 patients showed identical values of the histamine release measured by the two methods. It is noted that the sensitivity of the patient to the allergen is divided into classes were 0 means no reaction, while 3 represents the greatest reaction. Thus, the correlation applies to both nonallergic patients and all three classes of allergy.

EXAMPLE 3

In a modification of the method according to the foregoing Example 2, histamine is determined directly after binding to glass microfiber filters.

A: 10 $\mu$l of unlabelled histamine dissolved in Tris-AMC buffer, cf. Example 1 (800 ng-400 ng-200 ng-100 ng-50 ng and 0 histamine/ml Tris-AMC), are incubated for 40 min. at 37° C., followed by washing with $H_2O$ for 15 sec. in a cell harvester. Residual $H_2O$ is removed from glass microfiber discs of a diameter of 6 mm punched out of GF/B filters. Histamine bound to the discs is determined fluorometrically. Coupling is accomplished with 400 $\mu$l of NaOH/OPT (10 mg o-phthaldialdehyde (Fluka) dissolved in 5 ml of methanol and mixed with 18 ml of 0.05M NaOH) for 4 min. at room temperature. To stabilize the flourophore 400 $\mu$l of 0.175M $H_3PO_4$ is added. The samples are centrifuged at 2800 g for 10 min. Reading of the extinction is performed using an AMINCO fluorometer (see curve III in FIG. 5).

B: The following control is included: 10 $\mu$l of histamine in the same concentration as used in A are incubated with discs for 40 min. at 37° C. The samples are not washed in a cell harvester, but are immediately coupled as stated in A (see curve II in FIG. 5).

C: The following additional control is included: 10 $\mu$l of histamine in the same concentrations as used in A are incubated for 40 min. at 37° C. in the absence of discs. The samples are not washed in a cell harvester, but are immediately coupled as stated in A (see curve I in FIG. 3).

The three curves thus show:
I: total amount of histamine added to the test tubes.
II: total amount of histamine added to the filter discs in the test tubes.
III: histamine binding to the filter discs after washing.

Although this procedure is not optimized in the above examples, curve III clearly shows the fine linear correlation between the various histamine concentrations and the binding to the fibers.

What we claim is:
1. A method for detecting or determining histamine in body fluids which comprises:
   contacting a sample of the fluid with glass microfibers deposited onto a carrier in such quantitative proportions between the glass microfibers and the fluid as will permit the histamine amount to be detected or determined to be bound to the microfibers; and
   registering or measuring the bound amount of histamine.
2. The method according to claim 1 adapted as a competitive histamine detection or determination, which comprises:
   adding to a sample of body fluid possibly containing histamine prior to the contacting step a predetermined amount of labelled histamine,
   registering the amount of labelled histamine bound to the glass microfibers; and
   comparing the registered amount with a standard curve based on competition with known amounts of unlabelled histamine.
3. The method according to claim 1 or 2 for detecting histamine possibly released by allergic reaction in body fluids which comprises:
   adding a test allergen to the body fluid, and
   registering the possibly released histamine bound to the fibers.
4. The method according to claim 1, wherein the glass microfibers used are in the form of fine particles having dimensions ranging from 2 to 20 $\mu$m.

5. The method according to claim 1, wherein the glass microfibers used are boron silicate fibers sold under the trademark Whatman GF/B or fibers having similar binding properties.

6. The method according to claim 2, wherein the labelled histamine used is a radioactively labelled, fluorescent-labelled or enzyme-labelled histamine or histamine derivative.

* * * * *